(12) United States Patent
Falwell

(10) Patent No.: US 6,572,611 B1
(45) Date of Patent: *Jun. 3, 2003

(54) INTRACARDIAC GRASP CATHETER

(75) Inventor: Gary S. Falwell, Manchester, NH (US)

(73) Assignee: C. R. Bard, Inc., Murray Hill, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/434,599

(22) Filed: Nov. 5, 1999

Related U.S. Application Data

(63) Continuation-in-part of application No. 09/197,812, filed on Nov. 23, 1998, now Pat. No. 6,319,250.

(51) Int. Cl.[7] ............................................. A61B 18/14
(52) U.S. Cl. ........................ 606/41; 606/49; 606/50; 607/99; 607/113
(58) Field of Search ........................ 606/41, 49, 50; 607/99, 113

(56) References Cited

U.S. PATENT DOCUMENTS

| | | | | |
|---|---|---|---|---|
| 5,823,955 A | * | 10/1998 | Kuck et al. | 600/374 |
| 5,882,346 A | * | 3/1999 | Pomeranz et al. | 607/122 |
| 5,916,214 A | * | 6/1999 | Cosio et al. | 606/41 |
| 6,096,036 A | * | 8/2000 | Bowe et al. | 606/41 |
| 6,319,250 B1 | * | 11/2001 | Falwell et al. | 606/41 |

* cited by examiner

Primary Examiner—Lee Cohen
(74) Attorney, Agent, or Firm—Darby & Darby

(57) ABSTRACT

A method of treating cardiac arrhythmia, including guiding a distal end portion of a catheter, the distal end portion having a distal tip and accommodating an elongated configuration of ablation electrodes into a desired intracardiac region, for example, from the inferior vena cava into the right atrium of a human heart, and then from the right atrium into the right ventricle of the heart, pulling the catheter backwards, for example, towards the inferior vena cava, until the distal tip engages a edge of an intracardiac orifice, for example, the tricuspid annulus whereby the configuration of electrodes engages a target tissue, for example, the isthmus of tissue between the tricuspid annulus and the inferior vena cava, deflecting the distal tip into a hook-shaped configuration, and activating the configuration of electrodes to produce a substantially continuous lesion on the target tissue.

16 Claims, 7 Drawing Sheets

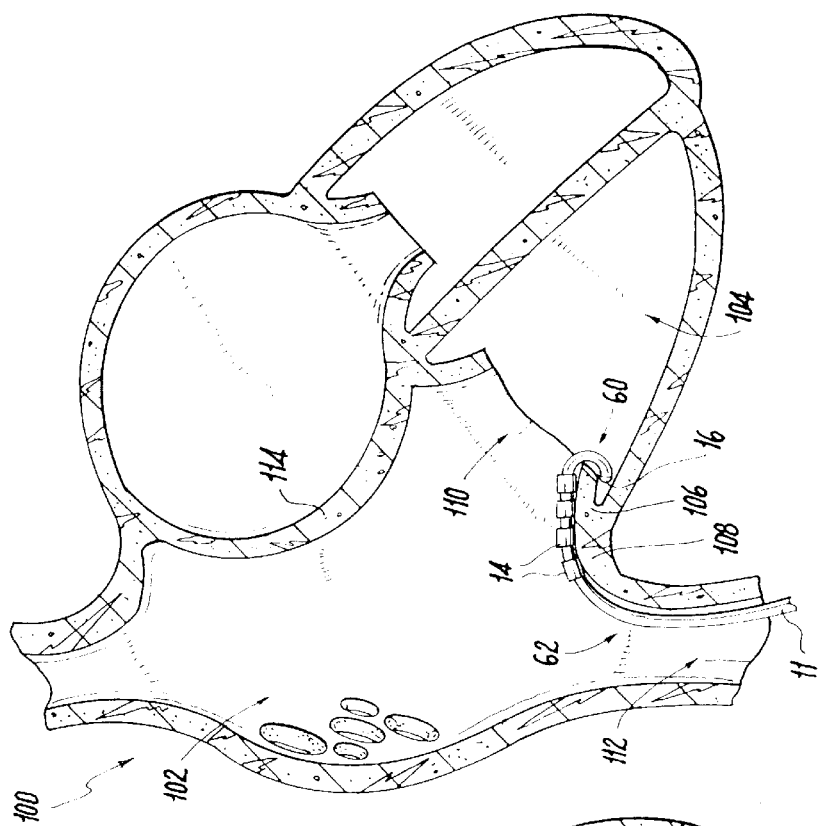
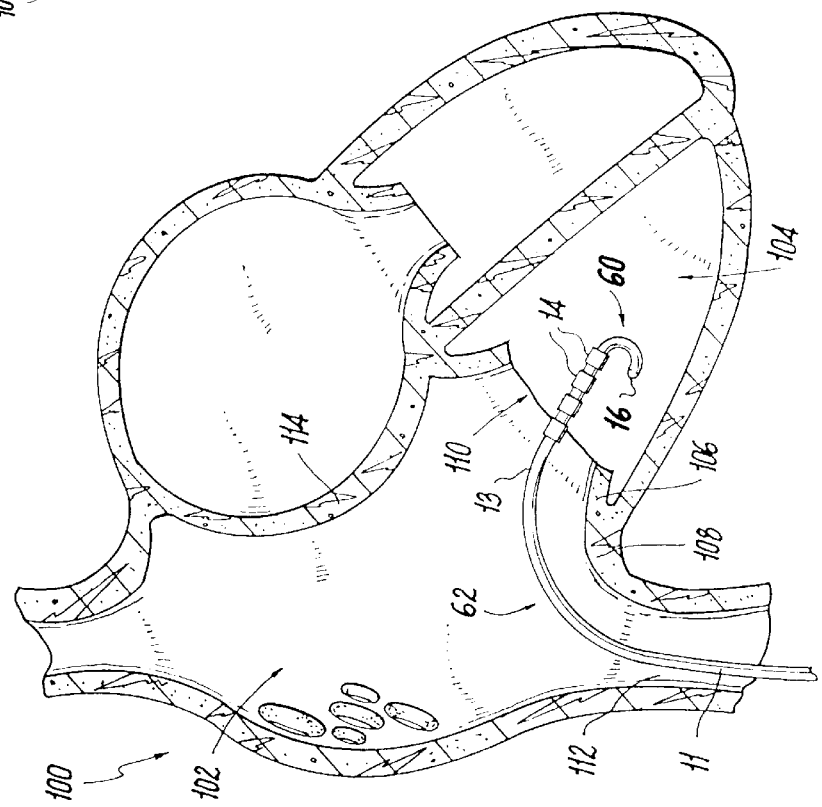

INTRACARDIAC GRASP CATHETER

RELATED APPLICATIONS

This application is Continuation-In-Part of U.S. patent application Ser. No. 09/197,812, filed Nov. 23, 1998, now U.S. Pat. No. 6,319,250.

FIELD OF THE INVENTION

The present invention relates to a steerable medical catheter and, more particularly, to a flexible, electrode-bearing catheter of the type used in electrophysiological studies for intracardiac electrocardiographic recording, mapping, stimulation and ablation.

BACKGROUND OF THE INVENTION

Catheters are often used in medical procedures to provide physical access to remote locations within a patient via a relatively small passageway, reducing the need for traditional invasive surgery. The catheter tube can be inserted into an artery or other passageway through a relatively small incision in the patient's body, and threaded through the patient's system of blood vessels to reach the desired target.

Various types of catheters are used in various procedures, both diagnostic and therapeutic. One general type of catheter used for both diagnostic and therapeutic applications is a cardiac electrode catheter. The diagnostic uses for a cardiac electrode catheter include recording and mapping of the electrical signals generated in the course of normal (or abnormal) heart function. Therapeutic applications include pacing, or generating and placing the appropriate electrical signals to stimulate the patient's heart to beat in a specified manner, and ablation. In an ablation procedure, electrical or radio-frequency energy is applied through an electrode catheter to form lesions in a desired portion of the patient's heart, for example the right atrium. When properly made, such lesions will alter the conductive characteristics of portions of the patient's heart, thereby controlling the symptoms of supra-ventricular tachycardia, ventricular tachycardia, atrial flutter, atrial fibrillation, and other arrhythmias.

Such a catheter is typically placed within a desired portion of the patient's heart or arterial system by making a small incision in the patient's body at a location where a suitable artery or vein is relatively close to the patient's skin. The catheter is inserted through the incision into the artery and manipulated into position by threading it through a sequence of arteries, which may include branches, turns, and other obstructions.

Once the cardiac electrode catheter has been maneuvered into the region of interest, the electrodes at the distal end of the catheter are placed against the anatomical feature or area sought to be diagnosed or treated. This can be a difficult procedure. The electrophysiologist manipulating the catheter typically can only do so by operating a system of controls at the proximal end of the catheter shaft. The catheter can be advanced and withdrawn longitudinally by pushing and pulling on the catheter shaft, and can be rotated about its axis by rotating a control at the proximal end. Both of these operations are rendered even more difficult by the likelihood that the catheter must be threaded through an extremely tortuous path to reach the target area. Finally, once the tip of the catheter has reached the target area, the electrodes at the distal end of the catheter are placed in proximity to the anatomical feature, and diagnosis or treatment can begin.

In the past, the difficulties experienced by electrophysiologists in the use of a cardiac electrode catheter have been addressed in a number of different ways.

To facilitate maneuvering a catheter through a tight and sinuous sequence of arterial or venous passageways, catheters having a pre-shaped curve at their distal end have been developed. To negotiate the twists and branches common in a patient's arterial or venous system, the catheter typically is rotatable to orient the pre-shaped curve in a desired direction. Although the tip of the catheter may be somewhat flexible, the curve is fixed into the catheter at the time of manufacture. The radius and extent of the curvature generally cannot be altered. Therefore, extensive pre-surgical planning is frequently necessary to determine what curvature of catheter is necessary. If the predicted curvature turns out to be incorrect, the entire catheter may need to be removed and replaced with one having the proper curvature. This is an expensive and time-consuming ordeal, as catheters are generally designed to be used only once and discarded. Moreover, the additional delay may place the patient at some additional risk.

A variation of the pre-shaped catheter uses a deflectable curve structure in the tip. This type of catheter has a tip that is ordinarily substantially straight, but is deflectable to assume a curved configuration upon application of force to the tip. However, the tip deflection is not remotely controllable. In a certain patient's arterial system, a point may be reached at which the proper force cannot be applied to the catheter tip. In such cases, the catheter must be withdrawn and reinserted through a more appropriate passage, or another catheter with a different tip configuration must be used.

Another attempt to facilitate the placement of catheters takes the form of a unidirectional steering catheter. A typical unidirectional steering catheter has a steering mechanism, such as a wire, that extends the length of the catheter to the distal tip. The steering mechanism is coupled to the tip in such a way that manipulation of the proximal end of the mechanism (e.g., by pulling the steering wire) results in deflection of the catheter tip in a single direction. This type of catheter is illustrated, for example, in U.S. Pat. No. 5,125,896 issued to Hojeibane. The direction of deflection can be controlled by embedding a ribbon of wire in the tip; the ribbon is flexible along one dimension but not in others. This type of catheter can further be controlled by rotating the entire shaft of the catheter; in this manner, the direction of bend within the patient can be controlled. The shaft of such a catheter must be strong enough to transmit torque for the latter form of control to be possible.

U.S. Pat. No. 5,383,852 to Stevens-Wright describes a steerable electrocardial catheter including a flexible tip assembly having a proximal and a distal section. In this catheter, two steering mechanisms are used to separately control bending of either or both the proximal and distal sections. The steering mechanisms for the proximal and distal sections include separate steering wires, as described above, which are coupled to the proximal and distal sections, respectively.

Bidirectional steering catheters also exist. The distal end of a bidirectional steering catheter can be maneuvered in two planes, allowing the tip to be positioned with greater accuracy. However, bidirectional steering catheters are complex mechanically and are often difficult to manipulate.

Although the foregoing types of catheters address the issue of maneuverability in different ways, none of them is ideally configured to maintain contact with and apply a desired amount of pressure to a desired anatomical feature, such as an atrial wall.

One device used for the latter purpose is known as a basket catheter. See, for example, the HIGH DENSITY MAPPING BASKET CATHETER manufactured by Cardiac Pathways Corporation. A basket catheter has several spring-biased arms near the distal tip. When these arms are unconstrained, they bow outward to define a basket-like shape. The arms of the basket are constrained for implantation in a sheath structure. When the tip of the catheter has reached the desired location, the sheath is retracted, or the arms are advanced out of the sheath.

However, because the tip of the catheter is sheathed, it is not easily steerable into location, and is not as flexible as one might desire. Moreover, the sheath adds bulk to the device, which might significantly limit the range of applications in which the basket catheter can be used. The basket has only one shape and size. Once the arms are deployed from the sheath, the basket assumes a single configuration defined upon manufacture. If the predefined configuration of the basket is not suitable, then substantially no correction is possible. Also, known basket catheters are not indicated for use in high-energy therapeutic applications, such as ablation.

A variable-geometry sheathed electrode catheter is also known in the art. This device has a single electrode-bearing tip portion that is initially disposed within a relatively inflexible sheath. When the tip portion is advanced with respect to the sheath, the tip portion bows out of a slot-shaped aperture in the sheath. The shape of the tip portion can be controlled to apply a desired amount of pressure to an anatomical feature. However, as a sheath is used around the catheter, the device is not easily steerable into location. Moreover, as discussed above, the sheath structure adds undesirable bulk to the device.

Radio frequency ablation (RFA) has become the treatment of choice for specific rhythm disturbances. To eliminate the precise location in the heart from which an arrhythmia originates, high frequency radio waves are generated onto the target tissue, whereby heat induced in the tissue burns the tissue to eliminate the source of arrhythmia.

For successful ablation treatment, e.g., to produce a lesion at a given anatomical site, it is generally required that the catheter be accurately positioned at the ablation site and that continuous contact be maintained between the electrode and the ablation site for the duration of the ablation treatment.

U.S. Pat. No. 5,617,854 to Munsif describes, inter alia, a pre-shaped catheter particularly useful for ablating in the vicinity of the sinoatrial node, the left atrium, and up to the mitral valve. The tip of the catheter is formed of a temperature-sensitive shape-memory material, e.g., Nitinol, or is otherwise invoked to assume a segmented configuration upon reaching a desired position. The segmented configuration includes a distal segment which bears an ablation electrode. In operation, the segmented shape produces tension which urges the ablation electrode on the distal segment into contact with a wall of the left atrium, while other segments are urged against other tissue. Since the shape of the catheter tip is fixed, the tip is not easily manipulated. Further, the tension produced between the segments of the catheter tip is dependent on the shape and dimensions of the ablation site, e.g., the left atrium.

Atrial fibrillation and atrial flutter are the most common type of arrhythmia found in clinical practice. Although the potential adverse consequences of these types of arrhythmia is well known, the basic electrophysiological mechanisms and certain management strategies to control these types of arrhythmia have been understood only recently.

Reference is made to FIG. 1 which schematically illustrates a cross-section of a human heart 100 showing typical atrial flutter circuits. Such circuits includes macro-entrant, counter-clockwise, pathways 120 from the right atrium 102, through the inter-atrial septum 114, down the free wall 116, and across the isthmus of tissue 108 between the inferior vena cava 112 and the tricuspid annulus 106 of the tricuspid valve 110.

Most electrophysiologists recommend treating atrial flutter by producing a linear contiguous lesion 118 at the isthmus of tissue 108, between vena cava 112 and the tricuspid annulus 106. Linear lesion 118 can be produced by RF ablation electrodes which are placed in contact with tissue 108. It is contemplated that isthmus tissue 108 is a critical link of the atrial flutter circuit and, thus, linear lesion 118 is expected to terminate this source of arrhythmia and prevent the recurrence of such arrhythmia.

Existing ablation treatment for atrial flutter includes the use of a catheter bearing at least one single or bi-polar ablation electrode. Unfortunately, an undue amount of time is spent in correctly positioning the ablation electrode of the catheter against the site to be treated. Further, in existing electrode catheter configurations, the catheter must generally be repeatedly repositioned until an acceptable lesion 118 is produced. Thus, lesion 118 is often non-continuous, i.e., there may be gaps in the lesion line which may require further repositioning of the ablation catheter. Such repeated repositioning of the catheter is time consuming and may result in prolonged, potentially harmful, exposure of patients to X-ray radiation.

Accordingly, there is a need for a cardiac electrode catheter that can be conveniently and quickly steered into secured, operative, engagement with a preselected portion of the isthmus of tissue between the inferior vena cava and the tricuspid annulus, to produce a predefined, substantially continuous, lesion on this isthmus of tissue.

The difficulties in steering, positioning and providing secured contact of an electrode catheter, with reference to the isthmus of tissue between the interior vena cava and the tricuspid annulus, are also applicable in mapping and/or ablating other intracardiac sites. For example, steering and positioning difficulties may arise in mapping and possible ablation in the vicinity of the coronary sinus.

SUMMARY OF THE INVENTION

The present invention seeks to provide a steerable electrode catheter having a relatively flexible distal end portion accommodating an elongated configuration of at least one ablation electrode, that can be conveniently guided to a predetermined intracardiac site, for example, to the vicinity of the tricuspid valve, and that can be steered into a shape which enables convenient positioning of at least one ablation electrode in secure operative engagement with predetermined mapping and/or ablation site, for example, an ablation site along the isthmus of tissue between the inferior vena cava and the tricuspid annulus. If ablation of tissue is required, an electrode catheter in accordance with the present invention may be used to produce a predefined, elongated, substantially continuous, lesion at the ablation site.

According to an embodiment of the present invention, the catheter includes a flexible distal end portion which may be controlled by one or two steering mechanisms, namely, a distal steering mechanism and/or a proximal steering mechanism. The distal steering mechanism may be adapted to deflect only the tip of the distal end portion into a hook-shaped configuration. The proximal steering mechanism may be adapted to deflect the entire distal end portion. Alternatively, the distal end portion of the electrode catheter may have a pre-shaped distal tip, e.g., the tip may be pre-shaped into a partly deflected configuration. In this alternative embodiment, a single steering mechanism may be used both to deflect the distal end portion and to further shape the pre-shaped distal tip into the desired hook-shaped configuration.

In another embodiment of the present invention, the distal end potion of the electrode catheter may be adapted to be steerable or deflectable at three regions, namely, a distal tip deflection region, an intermediate deflection region, and a proximal deflection region. The curvature of the distal end portion at the intermediate deflection region, in addition to either or both of the distal tip deflection region and the proximal deflection region, enables more flexibility in conforming the shape of the distal end portion of the catheter to the shape of the target tissue, e.g., the above mentioned isthmus of tissue, during mapping and/or ablation of the target tissue. In an embodiment of the present invention, the intermediate deflection region is adapted to be curved towards the target tissue, thereby to provide improved contact with the target isthmus when the end portion of the catheter is urged against the target tissue.

In yet another embodiment of the present invention, the distal end portion is not deflectable at the intermediate region but, rather, the distal end portion is formed of a resilient material and is pre-shaped to have a predetermined curvature at the intermediate region. In this embodiment of the invention, when the distal end portion is urged against the target tissue, the curvature of the intermediate region changes until the electrode configuration on the distal end potion conforms to the shape of the target tissue. This ensures urged contact between the at least one electrode and the target tissue without an additional steering mechanism.

According to an embodiment of the present invention, the at least one ablation electrode is brought into secured engagement with a target tissue, for example, the isthmus of tissue between the inferior vena cava and the tricuspid annulus, as follows. First, the distal end of the catheter is guided into the right atrium. As the distal end of the catheter advances in the right atrium, the proximal steering mechanism may be activated to deflect the entire distal end portion, such that the distal end portion may be conveniently inserted into the right ventricle. Once the distal end portion is inside the right ventricle, the distal steering mechanism is activated to produce the hook-shape configuration at the tip of the distal end portion. Then, the catheter is pulled back, i.e., in the direction of the right atrium, until the hook-shaped tip of the distal end is anchored at the tricuspid annulus. The catheter may then be pulled further back and the curvature of the distal end portion may be adjusted, e.g., using the proximal steering mechanism, until the at least one ablation electrode securely engages an ablation site along the isthmus of tissue between the tricuspid annulus and the inferior vena cava. Once such secured engagement is obtained, the at least one ablation electrode may be activated to produce a substantially continuous, linear, lesion at the ablation site.

As mentioned above, a catheter having a pre-shaped distal tip may alternatively be used. In such case, the catheter may be guided into the right ventricle and then pulled back until the pre-shaped tip is anchored at the tricuspid annulus, obviating the step of deflecting the distal tip before pulling back the catheter. The catheter may then be pulled further back and the curvature of the distal end portion may be adjusted, e.g., using the proximal steering mechanism, as described above, until the distal tip assumes the desired hook-shaped configuration that provides a firm grip of the tricuspid annulus and secure engagement between the at least one ablation electrode and the ablation site, e.g., along the isthmus of tissue between the tricuspid annulus and the inferior vena cava.

In other embodiments of the present invention, an electrode catheter configuration as described above may be used for mapping and/or ablation of tissue at other intracardiac location where anchoring onto an edge of an orifice may be helpful in correctly and securely positioning an electrode catheter. For example, a configuration as described above may be useful for mapping and, possibly, ablating of tissue in the vicinity of the coronary sinus, by maneuvering the distal end of the catheter into the coronary sinus and pulling the catheter back until the distal tip of the catheter is anchored at an edge of the coronary sinus orifice.

BRIEF DESCRIPTION OF THE DRAWINGS

The present invention will be understood and appreciated more fully from the following detailed description of the preferred embodiment taken in conjunction with the accompanying drawings in which:

FIG. 7 is a schematic, cross-sectional, illustration of the human heart, showing the tip of the electrode catheter of FIG. 2 being deflected into a "hook" shape;

FIG. 8 is a schematic, cross-sectional, illustration of the human heart, showing the electrode catheter of FIG. 2 being pulled back to engage the isthmus of tissue between the inferior vena cava and the tricuspid annulus with the tip of the catheter anchored at the tricuspid annulus;

DETAILED DESCRIPTION OF PREFERRED EMBODIMENTS

Figure 1:
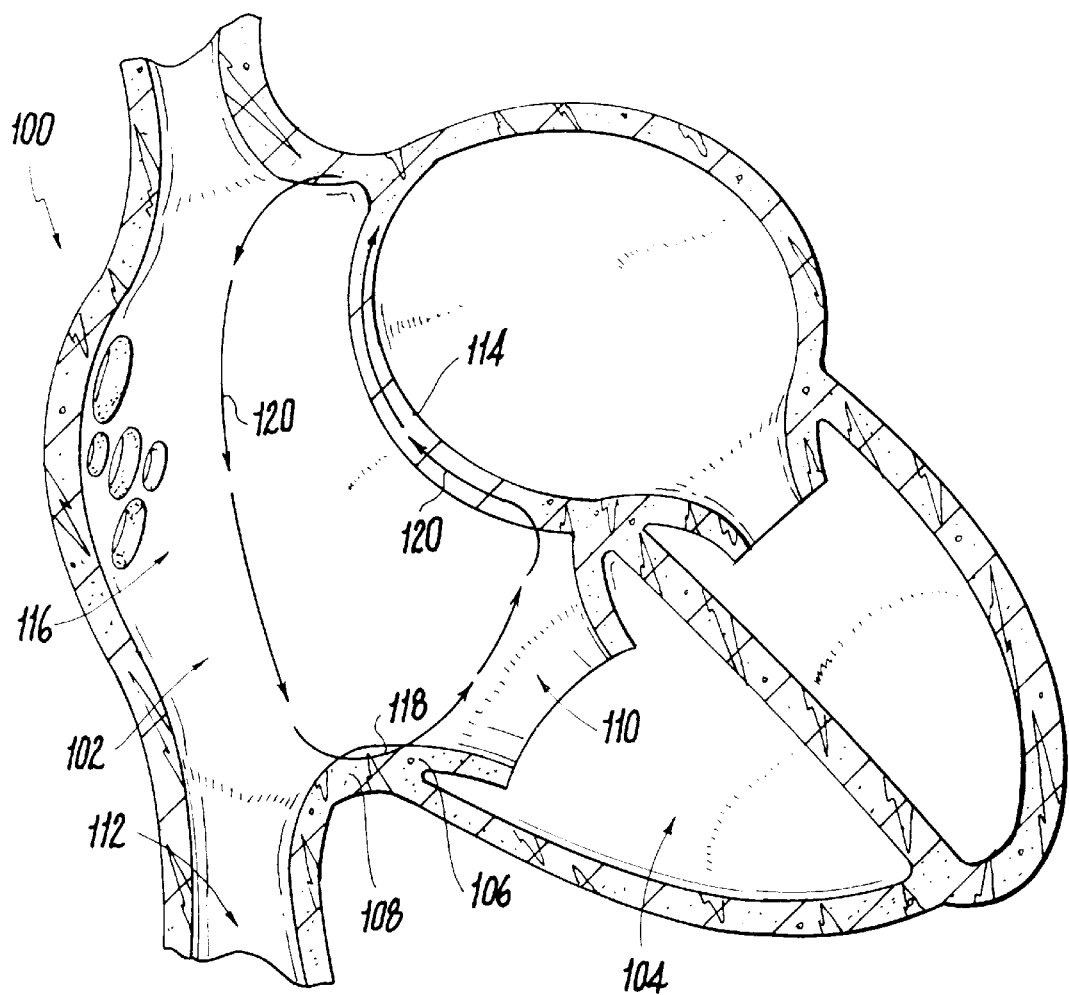
FIG. 1 is a schematic, cross-sectional, illustration of a human heart showing an atrial flutter circuit including an isthmus of tissue between the inferior vena cava and the tricuspid annulus.
Figure 2:
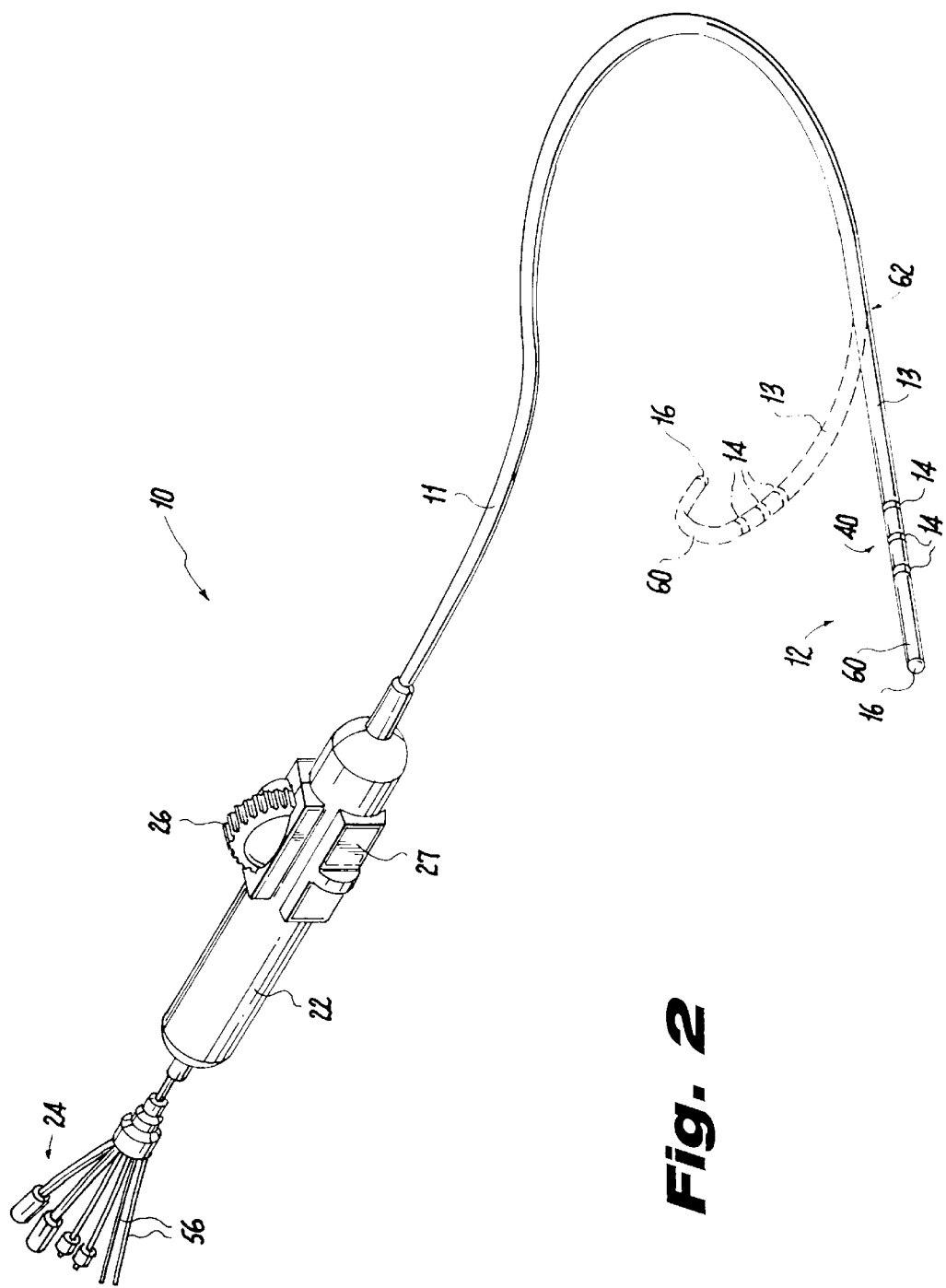
FIG. 2 is a schematic, cross-sectional, illustration of an electrode catheter in accordance with an embodiment of the present invention.

Reference is made to FIG. 2 which schematically illustrates a perspective view of an ablation and/or mapping catheter 10 in accordance with an embodiment of the present invention.

Catheter 10 includes a handle portion 22, electric connectors 24, a tubular catheter shaft 11 and a distal end portion 12 including an end shaft 13. Distal end portion 12 includes a distal tip 16, a distal tip deflection region 60 and a proximal deflection region 62. According to the present invention, distal end portion 12 can be steered from a generally straight configuration, indicated by the solid lines in FIG. 2, to a deflected configuration, indicated by the broken lines in FIG. 3. The broken line configuration in FIG. 2 also illustrates how distal deflection region 60 can be deflected into a hook-shaped configuration, as described in detail below.

In an embodiment of the present invention, tip 16 may include a sensor or mapping electrode, as is known in the art, for monitoring the electric potential of tissue in contact therewith. This may be helpful in guiding and positioning distal end portion 12, as described below. Additionally or alternatively, tip 16 may include an ablation electrode for ablating tissue in contact therewith.

Figure 3:
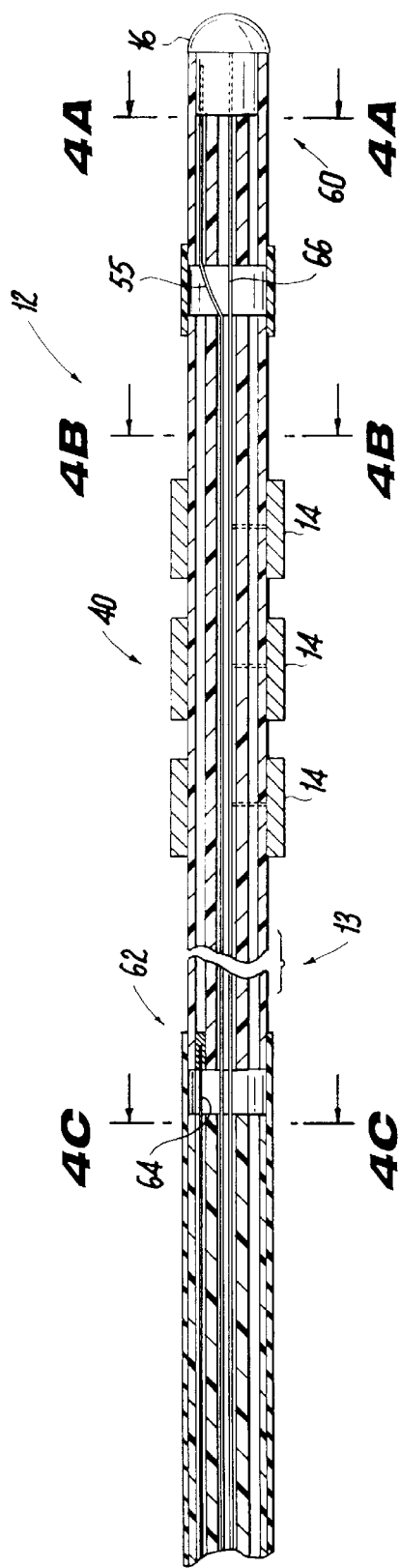
FIG. 3 is a schematic, side view, cross-sectional, illustration of a distal end portion of the electrode catheter of FIG. 2.

Reference is now also made to FIG. 3 which schematically illustrates a side-view, cross-section, of distal end portion 12. End shaft 13, which is preferably hollow as shown in FIG. 3, accommodates an elongated configuration 40 of ablation electrodes 14. Elongated configuration 40 may include any number of electrodes 14, with a predetermined spacing therebetween, or a single elongated electrode, as known in the art, adapted to produce a substantially continuous, substantially linear, lesion when brought into operative engagement with a target tissue. Electrodes 14 are preferably all ring-electrodes covering the entire circumference of shaft 13. Additionally or alternatively, electrodes configuration 40 may include at least one mapping electrode, as is known in the art, for monitoring the potential of the tissue in contact with the electrode configuration.

Figure 4A:
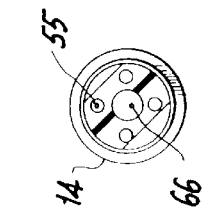
FIGS. 4A–4C are schematic, front view, cross-sections of the distal end portion of FIG. 3, taken along section lines A—A, B—B and C—C, respectively.
Figure 4B:
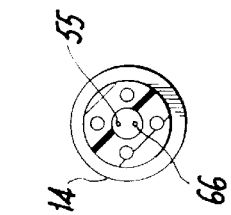
Figure 4C:
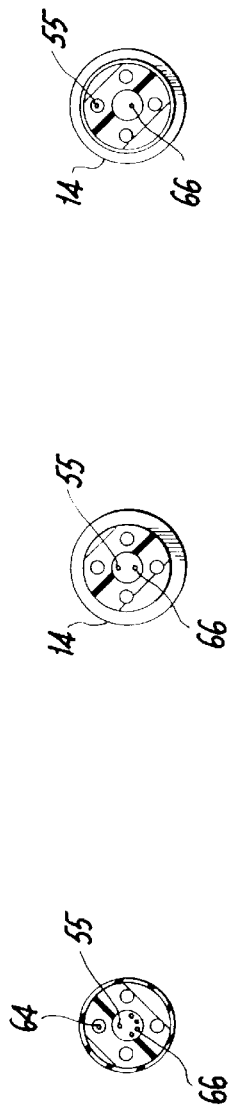

Reference is now made also to FIGS. 4A–4C which schematically illustrate front-view cross-sections of distal end portion 12 along section lines A—A, B—B, and C—C, respectively, in FIG. 3. In accordance with the present invention, catheter 10 includes a distal steering mechanism which is used to deflect tip 16 of distal end portion 12, as mentioned above, by producing a small radius of curvature at region 60. Catheter 10 further includes a proximal steering mechanism which controls the curvature of region 62, between shaft 11 and 13, thereby to control the deflection of the entire distal end portion 12.

The distal and proximal steering mechanisms may include any suitable steering mechanisms known in the art, for example, the control mechanisms described in U.S. Pat. No. 5,383,852 to Stevens-Wright, the disclosure of which is incorporated herein by reference. As shown in FIGS. 3–4C, the distal and proximal control mechanisms may include control wires 55 and 64, respectively, which extend along the interior of shaft 11 from handle portion 22 to regions 60 and 62, respectively, of distal end portion 12. Wire 55 is attached to tip 16 and may extend through middle guiding loops along most of the length of shaft 13, as shown in FIGS. 4B and 4C, and then through off-center guiding loops at region 60, as shown in FIG. 4A, whereby only a small segment adjacent to tip 16 is deflected by wire 55. Wire 64 may extends through off-center guiding loops in shaft 13, as shown in FIG. 4C, and is attached to end shaft 13 at region 62.

The deflection of distal end portion 12 into a desired configuration is preferably controlled by an electrophysiologist using control members 26 and/or 27 on handle portion 22. In the embodiment shown in FIG. 2, control member 26 may include a rotatable control member attached to wire 55, such that forward or backward rotation of control member 26 results in corresponding movement of wire 55, thereby controlling the deflection of end portion 12 at region 60. Control member 27 may include a slidable control member attached to wire 64, such that forward or backward sliding of control member 27 results in corresponding movement of wire 64, thereby controlling the deflection of end portion 12 at region 62. As known in the art, the electrophysiologist may also rotate distal end portion 12 about the longitudinal axis of catheter 10. Any suitable rotation mechanism, as is known in the art, can be used to control the rotation of distal end portion 12. For example, catheter shaft can be made of a rotationally rigid material that transmits the rotation of handle portion 22 to distal end 12. Alternatively, the rotation of handle 22 may be transmitted by a rotationally stiff member (not shown) extending longitudinally through the interior of catheter shaft 11.

In an embodiment of the present invention, electrodes 14 are addressed, together or separately, via connectors 24, which are connected to electrodes 14 by conductors 66. Conductors 66 may extend along the interior of catheter shaft 11 and end shaft 13, for example, through middle guiding loops, as shown in FIGS. 4A–4C.

Using connectors 24, electrodes 14 are connected to an ablation energizing circuit, which may be activated by user controls as are known in the art. Upon activation, the energizing circuit energizes electrodes 14 with radio frequency (RF) energy, as is known in the art. Using separate ablation controls, the electrophysiologist may activate electrodes 14 together or separately (if selective ablation is desired) to ablate a target tissue, as described in detail below.

As known in the art, electrodes 14 may be associated with temperature sensors (not shown in the drawings) which may be connected to temperature monitoring circuitry for monitoring the temperature of the tissue in contact with electrodes 14. An output of the temperature monitoring circuitry may be visually displayed to the electrophysiologist, as is known in the art, to provide the electrophysiologist with on-line indication of the electrode temperatures, which are indicative of adjacent tissue temperatures. If temperature sensors are used, they may be connected to the monitoring circuitry via connectors 56 and additional conductors (not shown) in catheter shaft 11.

According to the present invention, catheter 10 is used for ablating tissue on the endocardium isthmus of tissue between the inferior vena cava and the tricuspid annulus of a patient suffering from aberrant heart activity, such as atrial flutter or fibrillation, as described below.

FIGS. 5–8 schematically illustrate a procedure for introducing catheter 10 into the right atrium and subsequently guiding distal end portion 12 to securely engage a portion of the endocardium tissue 108 between the inferior vena cava and the tricuspid annulus.

Figure 6:
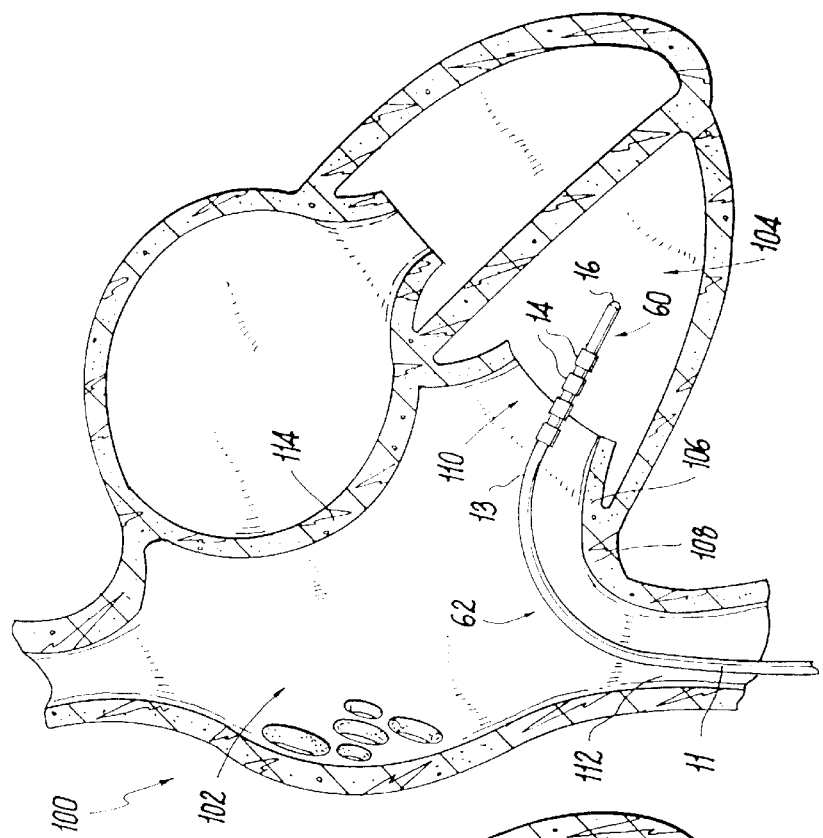
FIG. 6 is a schematic, cross-sectional, illustration of the human heart, showing the electrode catheter of FIG. 2 being steered from the right atrium into the right ventricle.
Figure 5:
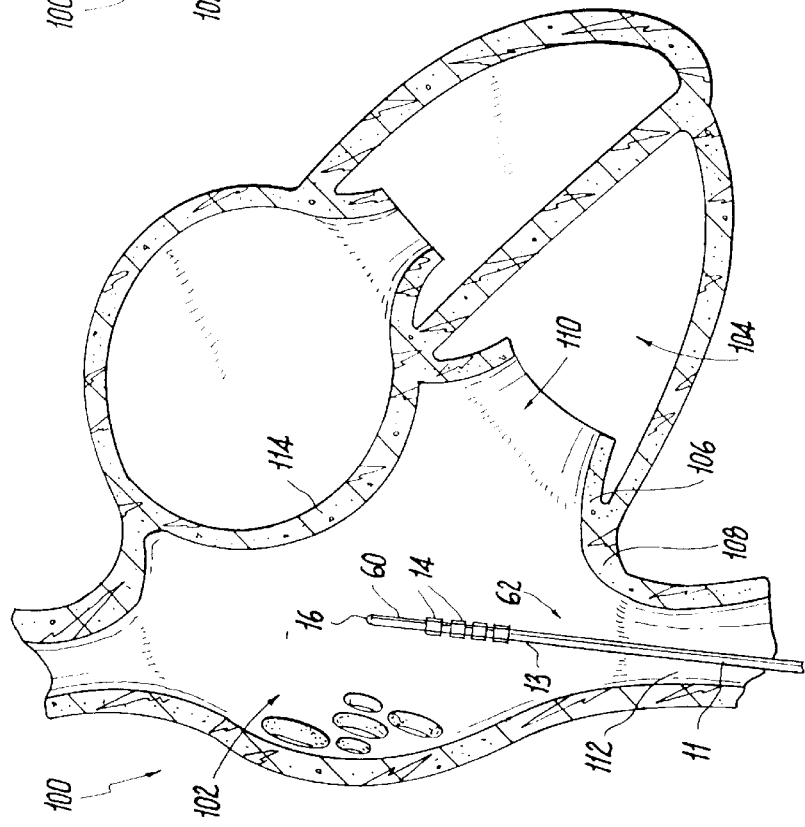
FIG. 5 is a schematic, cross-sectional, illustration of the human heart, showing the electrode catheter of FIG. 2 being introduced into the right atrium.

As shown in FIG. 5, distal end portion 12 is first guided into the right atrium of the patient's heart 100 from the inferior vena cava. Once catheter 10 is introduced into the right atrium, the electrophysiologist proceeds to deflect distal end portion 12 towards the right ventricle 104, using the proximal steering mechanism of catheter 10. Distal end portion 12 enters the right ventricle via the tricuspid valve 110, as shown in FIG. 6. If necessary, end shaft 13 may be rotated to assist in the manipulation of distal end portion 12.

After distal end portion 12 is inserted into the right ventricle, the electrophysiologist uses the distal steering mechanism to deflect tip 16 into the hook-shaped configuration described above, as shown in FIG. 7. Then, the catheter is pulled back, i.e., in the direction of inferior vena cava 112, until a portion of the tricuspid annulus 106 is grasped by the hook-shaped tip 16, as shown in FIG. 8.

Once tip 16 is anchored at the tricuspid annulus, the catheter may be pulled further back and the curvature of distal end portion 12 may be adjusted, using the proximal steering mechanism, until electrodes 14 of elongated configuration 40 securely engage a portion of the isthmus of tissue 108 between tricuspid annulus 106 and inferior vena cava 112. At this point, the electrophysiologist activates some or all of electrodes 14 to ablate a substantially continuous, substantially linear, lesion on the endocardial wall of the isthmus of tissue 108.

As described above, electrodes 14 may be associated with temperature sensors. These sensors may include thermocouples or any other temperature sensing means known in the art. Based on the temperatures measured by these optional temperature sensors, the electrophysiologist may deactivate some or all of electrodes 14 when the temperature of the ablated tissue site exceeds a predetermined threshold. Then, when the temperature of the ablated sites drops below the threshold, the electrophysiologist may reactivate electrodes 14 if further ablation is required.

As mentioned above, tip 16 may optionally include a sensor electrode for monitoring/mapping the electrical potential of tissue adjacent tip 16, e.g., to enable more accurate and/or more efficient positioning of end portion 12 against isthmus of tissue 108. Sensor electrodes may also be included in electrode configuration 40, e.g., for mapping the electrical potential along isthmus of tissue 108, during or between ablation sessions, to determine whether further ablation may be necessary.

Figure 9:
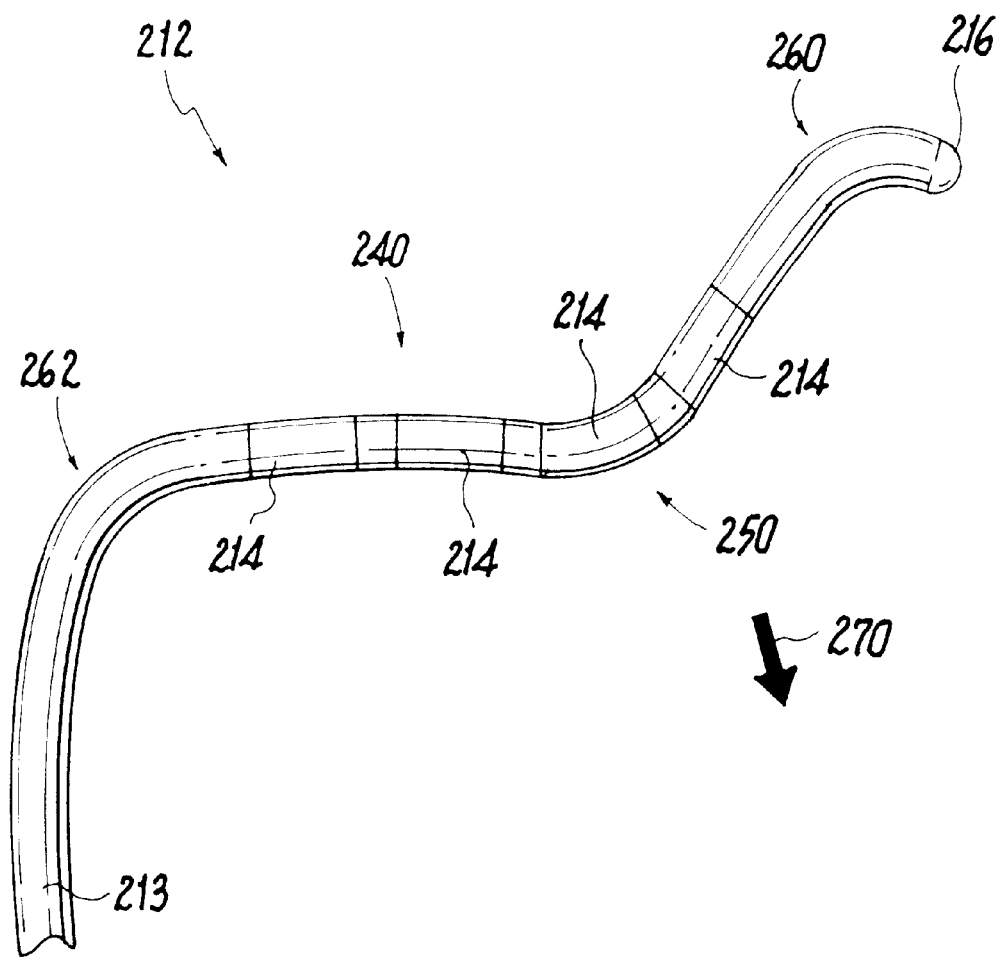
FIG. 9 is a schematic illustration of an end portion of an electrode catheter in accordance with another embodiment of the present invention.

Reference is now made to FIG. 9 which schematically illustrates a distal end portion 212 of an ablation catheter in accordance with another embodiment of the present invention, having an elongated electrode configuration 240 including a plurality of electrodes 214 and a tip 216. In the embodiment of FIG. 9, distal end potion 212 is adapted to be steerable or deflectable at three regions, namely, a distal tip deflection region 260, an intermediate deflection region 250 and a proximal deflection region 262. Regions 260 and 262 are generally analogous to the distal and proximal deflection regions 60 and 62, respectively, of distal end portion 12, as described above with reference to FIGS. 2–8. Intermediate deflection region 250 may be located at a predetermined position along electrode configuration 240. The mechanisms for deflecting end portion 212 at regions 260 and 262 may be similar to those used for deflecting end portion 12 at regions 60 and 62, respectively, as described in detail above with reference to FIGS. 2–8. The mechanism for deflecting distal end portion 212 at intermediate region 250 may include any suitable deflection mechanism, for example, a control wire (not shown) extending through the hollow interior of end portion 212, analogous to control wires 55 and 64 in the embodiment of FIGS. 2–8.

The curvature of end portion 212 at any or all of regions 260, 250 and 262 may be controlled by the electrophysiologist using any suitable controls (not shown), for example, handle controls similar to controls 26 and 27 in the embodiment of FIGS. 2–8. Thus, in this embodiment, the electrophysiologist may control the curvature of distal end portion 212 at region 250, in addition to controlling the curvature of distal and proximal regions 260 and 262. The addition of intermediate deflection region 250 enables more flexibility in conforming the shape of distal end portion 212 to the shape of isthmus of tissue 108 during ablation treatment. In an embodiment of the present invention, intermediate deflection region 250 is adapted to be deflected in the direction indicated by arrow 270, so as to provide improved contact with isthmus of tissue 108 when end portion 212 is urged against the tissue.

In yet another embodiment of the present invention, end portion 212 is not deflectable at region 250 but, rather, end portion 212 is formed of a resilient material and is pre-shaped to have a predetermined curvature at region 250, as shown generally in FIG. 9. In this embodiment of the invention, when end portion 212 is urged against a target tissue, such as isthmus of tissue 108, the curvature of region 250 changes until electrode configuration 240 conforms to the shape of the target tissue. This ensures urged contact between electrodes 214 and the target tissue without an additional steering mechanism.

In still another embodiment of the present invention, end portion 212 is deflectable only at distal region 260, to assume a hook-shaped configuration as described above, but is not deflectable at proximal region 262. End portion 212 may also be pre-shaped or deflectable at intermediate region 250, as described above. In this embodiment, once the tricuspid annulus is grasped by the hook-shaped tip of the catheter, it is primarily the backward pulling force applied by the electrophysiologist that brings electrodes 214 into urged contact with the target endocardial tissue.

Figure 10B:
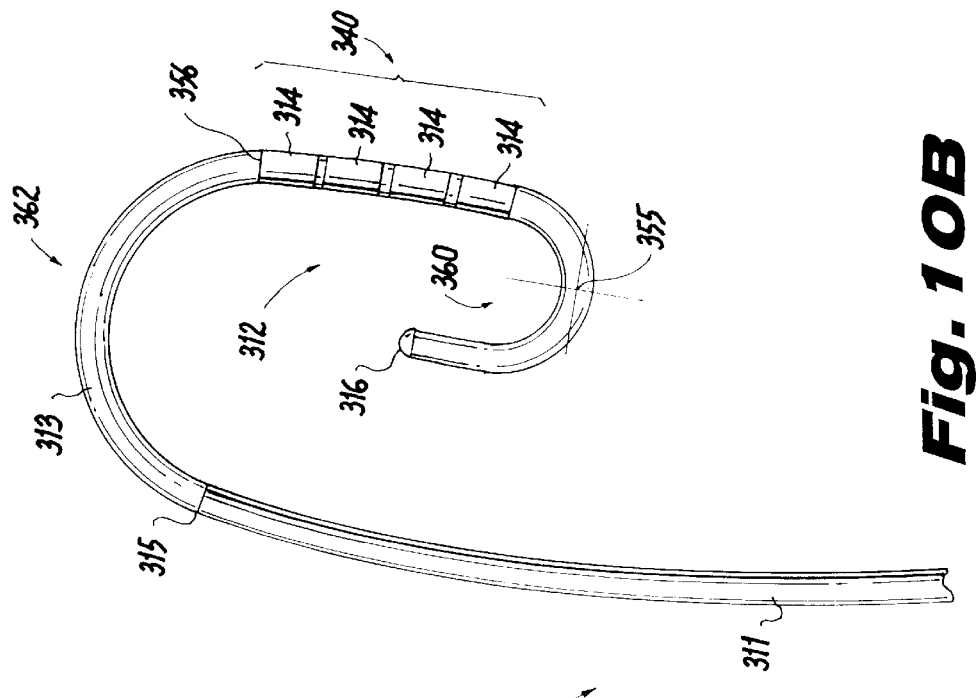
FIGS. 10A and 10B are schematic illustrations of part of an electrode catheter in accordance with yet another embodiment of the present invention, in a non-deflected configuration and a deflected configuration, respectively.
Figure 10A:
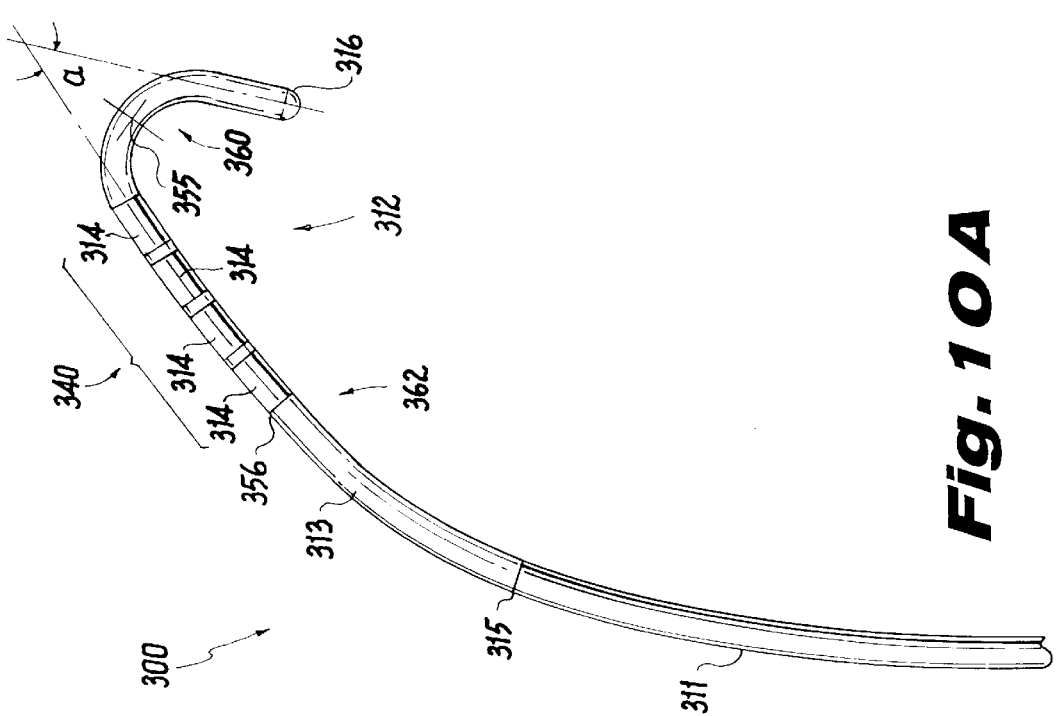

Reference is now made to FIGS. 10A and 10B which schematically illustrate part of an electrode catheter 300 in accordance with yet another embodiment of the present invention. Catheter 300 includes a tubular catheter shaft 311 and a distal end portion 312 including an end shaft 313. Distal end portion 312 includes a distal tip 316, a distal tip deflection region 360 and a proximal curvature region 362. In this embodiment, region 360 of distal end portion 312 is pre-shaped to have a partly deflected configuration, as shown in FIG. 10A, with an inner-curve angle α. Such pre-shaping of region 360 may be performed by pre-baking region 360 into the desired configuration, as is known in the art. As described below, distal end portion 312 may be steered into a deflected configuration, shown in FIG. 10B, wherein proximal curvature region 362 is curved to a predetermined extent and distal deflection region 360 is further deflected into a hook-shaped configuration, similar to that described above with reference to FIGS. 2–8.

Distal end portion 312 has an elongated electrode configuration 340 including a plurality of electrodes 314 and a tip 316. As in the embodiment of FIGS. 2–8, tip 316 may include a sensor or mapping electrode, as is known in the art, for monitoring the electric potential of tissue in contact therewith and/or an ablation electrode for ablating tissue in contact therewith. In the embodiment of FIGS. 10A and 10B, distal end potion 312 is adapted to be steerable or deflectable by a single deflection mechanism at both regions 362 and 360. The mechanism for deflecting end portion 312 at regions 360 and 362 may include a control wire (not shown), similar to control wire 55 in FIGS. 3 and 4A–4C, which extends through the hollow interior of end portion 312. The control wire is fixedly attached to tip 316 and may extend through off-center guiding loops, as are known in the art, along the entire length of shaft 313. Thus, in contrast to the embodiments described above with reference to FIGS. 2–8, the curvature of the entire length of distal end portion 312, including regions 362 and 360, is affected upon activation of the deflection mechanism, thereby producing the deflected configuration shown in FIG. 10B. re 55. In an embodiment of the present invention, shaft 313 is made from a material which is more flexible than the material used for shaft 311. The transition between the materials of shafts 311 and 313 is indicated by numeral-315. The material for shaft 313 may include Polyether Block Amide, having a Shore D hardness of 40–55, available from Atochem, Inc., U.S.A., under the trade name of Pebax. It should be appreciated, however, that wide range of materials and hardnesses of shaft 313 may be suitable for the present invention, depending on specific design requirements. The material used for shaft 311 should be at least slightly harder than that of shaft 313, and preferably has a Shore D hardness at least 5 higher than that of shaft 313.

It should be appreciated that, in the embodiment of FIGS. 10A and 10B, when the control wire is pulled backwards to deflect end portion 312, region 362 becomes curved and region 360 is fully deflected into the desired hook-shaped configuration, as shown in FIG. 10B. Thus, the deflection of both regions 362 and 360 is performed in a single action, obviating the need to use two separate deflection mechanisms, as in some of the above described embodiments. This simplifies the deflection procedure to be executed by the electrophysiologist.

Catheter 300 may be used for mapping and/or ablating the isthmus of tissue between the inferior vena cava and the tricuspid annulus, as follows. In analogy to the procedure described above with reference to FIGS. 5–8, distal end portion 312 is first guided into the right atrium of the patient's heart from the inferior vena cava. Once end portion 312 is introduced into the right atrium, the electrophysiologist proceeds to steer distal end portion 312 towards the right ventricle, using the single steering mechanism described above. Distal end portion 312 enters the right ventricle via the tricuspid valve, in analogy to the description above with reference to FIG. 6. If necessary, end shaft 313 may be rotated by the electrophysiologist to assist the manipulation of distal end portion 312.

Since distal end portion 312 is inserted into the right ventricle with a partly deflected distal deflection region 360, there is no need to further deflect the distal end portion before anchoring tip 316 at the tricuspid annulus. The electrophysiologist then simply pulls back the catheter, in the direction of the inferior vena cava, until a portion of the tricuspid annulus is grasped by the partly deflected tip 16, in analogy to the description above with reference to FIG. 8.

It has been found by the present inventors that when distal deflection region 360 is pre-shaped to be partly deflected by an inner-curve angle, α, of between about 20 degrees and about 100 degrees, for example, 40–60 degrees, regions 360 and 362 assume a final configuration (upon deflection), as shown in FIG. 10B, which is suitable for mapping and/or ablating tissue in the vicinity of the tricuspid annulus as described above. This finding is empirical and may depend on various parameters and specific applications design requirements of catheter 300. For example, the choice of angle α may depend on the material used to form shaft 313, the distance between transition point 315 and the proximal end of electrode configuration 340 (indicated by numeral 356), the distance between the center of region 360 (indicated by numeral 355) and distal tip 316, and/or the length of electrode configuration 340. For example, an angle of 40–60 degrees has been found suitable for a distal end portion 312 made from the Pebax material described above, wherein the distance between transition 315 and proximal electrode 356 is approximately 3.5 cm, the distance between center 355 and tip 316 is approximately 1.8 cm, and the length of electrode configuration 340 is approximately 2.8 cm.

Once tip 316 is anchored at the tricuspid annulus, the catheter may be pulled further back and the deflection mechanism described above may be used to further curve region 362 and to fully deflect region 360 into the hook-shaped configuration shown in FIG. 10B, until electrodes 314 of elongated configuration 340 securely engage a portion of the isthmus of tissue between tricuspid annulus and inferior vena cava. At this point, the electrophysiologist may activate some or all of electrodes 314 to ablate a substantially continuous, substantially linear, lesion on the endocardial wall, as described above.

It should be understood that electrode catheter configurations as described above may also be used for mapping and/or ablation of other intracardiac sites where anchoring onto an edge of an orifice may be helpful in correctly and securely positioning an electrode catheter. For example, a configuration as described above may be useful for mapping and, possibly, ablating tissue in the vicinity of the coronary sinus, by maneuvering the distal end of the catheter into the coronary sinus and subsequently pulling the catheter back until the distal tip of the catheter is anchored at an edge of the coronary sinus orifice.

It will be appreciated by persons skilled in the art that the present invention may be carried out using any of the above described configurations of electrodes and/or deflection regions and/or pre-shaped regions, as well as any other suitable configuration of electrodes and/or deflectable/pre-shaped regions.

It should be appreciated that the present invention is not limited to the specific embodiments described herein with reference to the accompanying drawing.

Rather, the scope of the present invention is limited only by the following claims:

1. A catheter for mapping and/or ablating tissue comprising:
   a body portion;
   a distal end portion having a distal tip and including a plurality of distal end portion electrodes proximal to said distal tip, said distal end portion electrodes adapted to produce a substantially continuous, elongated, lesion in said tissue when energized with radio frequency (RF) energy;
   a proximal deflection mechanism for deflecting substantially the entire length of said distal end portion in a predetermined direction and including at least a portion of the length of said proximal deflection mechanism located inside said body portion wherein said proximal deflection mechanism is a first pull wire;
   a distal deflection mechanism for deflecting a region of said distal end portion including said distal tip in said predetermined direction, from a generally straight configuration into a hook-shaped configuration, and at least a portion of said distal deflection mechanism being located inside said body portion, wherein said distal deflection mechanism is a second pull wire and wherein said distal end portion electrodes are located proximal to the region deflected by said distal deflection mechanism; and
   an intermediate steering mechanism which controls the curvature of a region of said distal end portion along said plurality of distal end portion electrodes.

2. A catheter according to claim 1 wherein a region near the distal tip of the distal end portion is pre-shaped to assume a first configuration.

3. A catheter according to claim 2 wherein said first configuration is a partly deflected configuration.

4. A catheter according to claim 3 wherein said region near the distal tip of the distal end portion, in said partly deflected configuration, has an inner-curve angle of between about 20 degrees and about 100 degrees.

5. A catheter according to claim 1 wherein said tissue comprises an isthmus of tissue between the tricuspid annulus and the inferior vena.

6. A catheter for ablating intracardiac tissue comprising:
a body portion;
a distal end portion having a distal tip and accommodating an elongated configuration of ablation electrodes adapted to produce a substantially continuous, elongated, lesion in said tissue when energized with radio frequency (RF) energy;
a distal steering mechanism which controls the curvature of a region of said distal end portion near said distal tip,
wherein said distal steering mechanism is adapted to deflect said distal tip from a first, generally straight, configuration into a second, hook-shaped, configuration;
a proximal steering mechanism which controls the curvature of a proximal region of said distal end portion, wherein said proximal steering mechanism is adapted to deflect substantially the entire length of said distal end portion; and
an intermediate steering mechanism which controls the curvature of a region of said distal end portion along said configuration of electrodes.

7. A catheter for ablating intracardiac tissue comprising:
a body portion;
a distal end portion having a distal tip and accommodating an elongated configuration of ablation electrodes adapted to produce a substantially continuous, elongated, lesion in said tissue when energized with radio frequency (RF) energy;
a distal steering mechanism which controls the curvature of a region of said distal end portion near said distal tip,
wherein said distal steering mechanism is adapted to deflect said distal tip from a first, generally straight, configuration into a second, hook-shaped, configuration;
a proximal steering mechanism which controls the curvature of a proximal region of said distal end portion, wherein said proximal steering mechanism is adapted to deflect substantially the entire length of said distal end portion wherein the distal end portion includes a pre-shaped, curved region at a predetermined location along said elongated configuration of electrodes.

8. A catheter according to claim 7 and further comprising an intermediate steering mechanism which controls the curvature of a region of said distal end portion along said configuration of electrodes.

9. A catheter for mapping and/or ablating tissue comprising:
a body portion;
a distal end portion having a distal tip and including a plurality of distal end portion electrodes proximal to said distal tip, said distal end portion electrodes adapted to produce a substantially continuous, elongated, lesion in said tissue when energized with radio frequency (RF) energy, said distal tip including a distal tip electrode;
a proximal deflection region between said body portion and said distal end portion;
a distal deflection region near the distal tip of said distal end portion and in between said distal end portion electrodes and said distal tip electrode;
a first pull wire having a proximal end and a distal end, said distal end of said first pull wire being connected to a first point inside said distal tip and said first point being radially remote from a point on the central axis of said catheter;
a second pull wire having a proximal end and a distal end, said distal end of said second pull wire being connected to a second point inside said proximal deflection region and said second point being located on an axis which is parallel to the central axis of the catheter and on which the first point is located, whereby deflection of the proximal deflection region and the distal deflection region are in the same direction; and
wherein said region near the distal tip of the distal end portion is pre-shaped to assume a first configuration.

10. A catheter according to claim 9 wherein said first configuration is a partly deflected configuration.

11. A catheter according to claim 10 wherein said region near the distal tip of the distal end portion, in said partly deflected configuration, has an inner-curve angle of between about 20 degrees and about 100 degrees.

12. A catheter according to claim 9 wherein said tissue comprises an isthmus of tissue between the tricuspid annulus and the inferior vena.

13. A method of treating cardiac arrhythmia, comprising:
guiding a distal end portion of a catheter, the distal end portion having a distal tip and accommodating an elongated configuration of ablation electrodes, from the inferior vena cava into the right atrium of a human heart;
guiding said distal end portion from the right atrium into the right ventricle of said heart;
pulling said catheter towards the inferior vena cava until said distal lip engages the tricuspid annulus of said heart and said configuration of electrodes engages the isthmus of tissue between the tricuspid annulus and the inferior vena cava of said heart;
deflecting said distal tip into a hook-shaped configuration; and
activating said configuration of electrodes to produce a substantially continuous lesion on said isthmus of tissue.

14. A method according to claim 13 wherein guiding said distal end portion from the right atrium into the right ventricle includes deflecting said catheter at a proximal region of said distal end portion.

15. A method of treating cardiac arrhythmia and/or mapping intracardiac tissue, comprising:
guiding a distal end portion of a catheter, the distal end portion having a distal tip and accommodating an elongated configuration of electrodes into an intracardiac region;
pulling said catheter backwards until said distal tip engages an edge of an intracardiac orifice and said configuration of electrodes engages a target tissue in the vicinity of said intracardiac orifice;
deflecting said distal tip into a hook shaped configuration; and
mapping and/or ablating a portion of said target tissue using said configuration of electrodes.

16. A method according to claim 15 wherein guiding said distal end portion comprises deflecting said catheter at a proximal region of said distal end portion.

* * * * *